United States Patent [19]

Neville, Jr. et al.

[11] 4,359,457

[45] Nov. 16, 1982

[54] ANTI THY 1.2 MONOCLONAL ANTIBODY-RICIN HYBRID UTILIZED AS A TUMOR SUPPRESSANT

[76] Inventors: David M. Neville, Jr., 9624 Parkwood Dr., Bethesda, Md. 20014; Richard J. Youle, 9629 Old Spring Rd., Kensington, Md. 20795

[21] Appl. No.: 186,735

[22] Filed: Sep. 30, 1980

[51] Int. Cl.³ ..................... A61K 39/44; A61K 45/05; G01N 33/68

[52] U.S. Cl. ................................ 424/85; 260/112 R; 260/121; 424/12; 424/88; 424/101; 424/177

[58] Field of Search ................ 424/8, 12, 85, 88, 101, 424/177; 260/112 R, 112 B, 121

[56] References Cited

PUBLICATIONS

Neville, et al. Biochemical Soc., London, Transactions, vol. 8 No. 6, 1980 pp. 692–693.

Moolten et al., Proc. Amer. Asso. for Cancer Res., Abstracts, vol. 15 1974, p. 24, Ab. No. 94.

Jansen et al., Immunobiology, vol. 157, No. 3, 1980 pp. 229–230.

Youle et al., Proc. Natl. Acad. Sci., vol. 77, No. 9, Sep., 1980 pp. 5483–5486.

Saxena et al., Immunological Communications, vol. 9, No. 4, 1980 pp. 371–378.

Youle et al., Proc. Natl. Acad. Sci., USA, vol. 76, 1979 pp. 5559–5562.

*Primary Examiner*—Anna P. Fagelson

*Attorney, Agent, or Firm*—John S. Roberts, Jr.

[57] ABSTRACT

A tumor suppressive composition active against lymphoma consisting of an injection of hybrid protein anti Thy 1.2 monoclonal antibody-ricin and hyperosmotic lactose. The inoculation i.v. of murine tissues in vivo by lymphoma is made at −20 to −25 days and the tumor suppressant composition is used i.v. at Day 1 in an amount of 1–3 μg of anti Thy monoclonal antibody-ricin together with sufficient hyperosmotic lactose to raise the lactose level to 20–30 mM. The broad purpose of this invention is to modify the receptor specificity of a potent toxin such as ricin by coupling it with a monoclonal antibody directed at a specific tumor or differentiation antigen. The object here is to use the reagent to selectively kill tumor cells without affecting normal cells.

3 Claims, No Drawings

ANTI THY 1.2 MONOCLONAL ANTIBODY-RICIN HYBRID UTILIZED AS A TUMOR SUPPRESSANT

This invention relates to a tumor suppressive composition active against lymphoma consisting of an injection of hybrid protein anti Thy 1.2 monoclonal antibody-ricin and hyperosmotic lactose. The inoculation i.v. of murine tissues in vivo by lymphoma is made at −20 to −25 days and the tumor suppressant composition is used i.v. at Day 1 in an amount of 1–3 μg of anti Thy monoclonal antibody-ricin together with sufficient hyperosmotic lactose to raise the lactose level to 20–30 mM. The broad purpose of this invention is to modify the receptor specificity of a potent toxin such as ricin by coupling it with a monoclonal antibody directed at a specific tumor or differentiation antigen. The object here is to use the reagent to selectively kill tumor cells without affecting normal cells.

The purpose of this invention is to modify the receptor specificity of a potent toxin such as ricin by coupling it with a monoclonal antibody directed at a specific tumor or differentiation antigen. The object generally is to use this reagent to selectively kill human tumor cells without affecting normal cells.

A number of attempts have been made to develop tumor specific cytotoxic reagents by coupling antitumor antibodies to toxins. Early studies failed to show large selectivity between tumor cells and normal cells because (1) toxin binding to normal cells via toxin B chain was not blocked and (2) polyclonal antibodies raised in xenogenic animals have broad specificity and react with normal cells (*Science,* 169:68–70, 1970; *J. Natl. Cancer Inst.,* 55:473–477, 1975; *Nature,* 271:752–755, 1978).

However, in order to overcome toxin binding to normal cells via the toxin B chain, conjugates with antibody and toxin A chains have been attempted (the toxin A chain is what kills the cell if it can get to the right intracellular compartment). A chain-antibody conjugates showed cell type specificity but low overall toxicity (*Biochem. Biophys. Res. Comm.,* 90:320–326, 1979).

These antibody toxin conjugates use the entire toxin since it is shown that the toxin B chain contains a necessary entry function in addition to its usual binding function. The toxin ricin is bound to normal cells with lactose. In animals studies antibody-ricin conjugates are given intravenously in hyperosmotic lactose, sufficient to raise serum lactose to 20–30 mM. The entry function on the toxin B chain is at an intracellular site not accessible to lactose. Therefore, the entry function is maintained and the antibody toxin conjugate in the presence of lactose has the same toxicity as ricin alone toward the target cell. To insure a high degree of tumor specific selectivity, antibodies are of monoclonal origin.

USE STATEMENT

This invention is a test or kit with some human useful linkage which utilizes an antibody toxin conjugate where the entire toxin is utilized and it is shown that the toxin B chain contains a necessary entry function in addition to its usual binding function. In animal studies antibody ricin conjugates are given intravenously in hyperosmotic lactose sufficient to raise the serum lactose to 20–30 mM.

PRIOR ART STATEMENT

Youle et al, *Proc. Natl. Acad. Sci.,* 76(11):5559–5562, November 1979.

Youle et al, "Anti-Thy 1.2 Monoclonal Antibody Linked to Ricin is a Potent Cell Type Specific Toxin," in press, *Proc. Natl. Acad. Sci.*

Köhler et al, *Nature,* 256:495–497, Aug. 7, 1975.

Masuho et al, *Biochem. Biophys. Res. Comm.,* 90(1):320–326, Sept. 12, 1979.

Moolten et al, *Science,* 169:68–70, 1970.

Thorpe, et al, *Nature,* 271:752–754, February 1978.

It can be shown in Example 4, post, that potent cell type specific toxins can be made by the proper alteration of toxin binding specificity. A monoclonal antibody can be used as the receptor binding moiety of a hybrid toxin and will define the hybrid cell type specificity. By coupling Thy 1.2 specific monoclonal antibody to ricin and blocking the ricin galactose binding site with lactose, the receptor specificity of ricin is altered. Under these conditions the new reagent, anti-Thy 1.2-ricin, is 700 times more toxic to T-cells which contain the Thy 1.2 surface antigen than to cells lacking it. This degree of selectivity can allow one to kill antigen bearing cells and not other cells in tissue culture. This differential of toxicity may be sufficient to selectively kill antigen bearing cells in vivo.

Several studies of toxins or their subunits linked to polyclonal antibodies, hormones, and lectins have been reported. These hybrids, though generally showing altered receptor specificity of the toxins, have very low potency compared to the native toxins. The M6P-ricin and anti-Thy 1.2-ricin hybrids prepared in this invention maintain the high potency of the toxin. The mild and specific coupling methods of this invention play a role in maintaining high toxin potency. More important perhaps is the inclusion of the ricin B chain within the hybrid. The ricin B chain performs an entry function which is independent of ordinary ricin binding to surface galactose receptors (Youle et al, *Proc. Natl. Acad. Sci.,* 76:5559–5562, 1979). If a wide variety of high potency monoclonal antibody hybrids can be made irrespective of the antigen receptor specificity, the ricin B chain entry function becomes more important. Alternatively, it is possible that the high degree of selective cytotoxicity elicited by Thy 1.2-ricin is dependent on unique features inherent in the Thy 1.2 antigen.

Since the M6P-ricin and anti-Thy 1.2-ricin hybrids contain the ricin B chain, these hybrids require the presence of lactose to block the ricin B chain binding to achieve cell type specificity. This limits the presently achievable selectivity between cell types to between 30- and 700-fold. Naturally occurring toxins which utilize receptor mediated protein transport systems can exhibit cell type selectivities up to 10,000-fold. This degree of selectivity could in principle be also reached by antibody-toxin hybrids of the proper construction. The currently available selectivity, however, is more than ample for the use of hybrids as selective agents for the isolation of receptor minus mutant cell lines. It may be possible to efficiently select for variants that lack any cell surface components toward which an antibody can be raised. This approach avoids utilization of complement dependent cell lysis.

The use of monoclonal antibodies as the cell recognition moiety of toxin hybrids greatly expands the possible uses of antibody-toxin hybrids. Several cell-type specific and tumor specific or tumor associated monoclonal antibodies have been produced. Hybrids of ricin with these antibodies would kill the antigen bearing cells selectively. There is considerable scientific and pharmacologic potential for these potent monoclonal antibody-ricin hybrids as cell type and tumor specific toxins.

GENERALIZED TEACHING OF PROCESS

There was previously reported the construction of a cytotoxic reagent specific for murine T cells carrying the differentiation antigen Thy 1.2 and tumor lines derived from such T cells. This reagent was constructed by linking the toxin ricin to a monoclonal antibody directed against the Thy 1.2 antigen. This procedure provided the toxin with a new receptor binding activity specific for the Thy 1.2 antigen. Ricin binding and toxicity by its usual uptake mechanism was inhibited by blocking the ricin galactose site with lactose. In tissue culture anti-Thy 1.2-ricin selectively killed EL-4 leukemia cells carrying the Thy 1.2 antigen while failing to kill AKR cells which lacked the Thy 1.2 antigen. In order to produce equivalent killing of AKR cells, a 700-fold increase on anti-Thy 1.2-ricin was required.

The present invention shows that the selective cell killing of anti-Thy 1.2-ricin in the presence of lactose can be utilized to prolong the lives of B6 mice carrying EL-4 syngeneic tumors. Lactose is supplied to the extracellular fluid space simultaneously with anti-Thy 1.2-ricin by intravenous injection.

C57BL/6 mice were inoculated with $7\times10^6$ EL-4 cells. Twenty-three days later mice were selected whose average long axis tumor diameter was 2.5 cm. These mice were divided into 5 treatment groups containing 4–6 animals each. The average size of the tumors (long$\times$short axis) was $4.1\pm1.5$ $cm^2$ with a range of 2.5–8.3 $cm^2$ and the average size of each group was within the standard error. On Day 23 each treatment group was injected via a tail vein with 300 $\mu$l of 0.75 M lactose in phosphate buffered saline and containing either 3, 2, or 1 $\mu$g of anti-Thy 1.2-ricin, 0.15 $\mu$g ricin, or 0.05 $\mu$g ricin. Mice were inspected and weighed daily and deaths were tabulated.

MATERIALS AND METHODS

Ricin was purified from seeds of *Ricinus communis.* L-[U-$^{14}$C]leucine in 0.01 N HCl (290 mCi/mmole) was from New England Nuclear, and m-maleimidobenzoyl-N-hydroxysuccinimide ester was from Pierce Chemical Co. Mouse thymic leukemia cells, EL-4, of B6 background were supplied by the National Institute of Allergy and Infectious Diseases, AKR-K36 thymic leukemia cells by the Fred Hutchinson Research Center, and AKT8, a spontaneous thymoma from AKR mice by Johns Hopkins University. Monoclonal antibody specific for Thy 1.2 mouse T cell antigen, clone 30-H12 derived by Ledbetter and Herzenberg (Immunol. Rev., 47:63–90(1979)) was purchased from Becton Dickinson, Mountain View, Calif. The hybridoma was generated by fusion of the mouse myeloma line NS1 with spleen cells of LOU/Ws1/M rats immunized with SJL (Thy 1.2) mouse spleen cells. This xenogeneic antibody is highly reactive against mouse cells carrying the Thy 1.2 alloantigen but nonreactive against thymocytes of AKR mice carrying the Thy 1.1 allele.

EXAMPLE 1

C57BL/6 mice injected subcutaneously with $7\times10^6$ EL-4 lymphoma cells 23 days earlier were treated by intravenous injection of the hybrid protein anti-Thy 1.2 monoclonal antibody-ricin and hyperosmotic lactose. Control animals received ricin and hyperosmotic lactose. Average tumor weight at treatment was 6 grams. Mean survival times of control groups following treatment were 6 and 8 days while groups receiving 2 and 3 $\mu$g of hybrid were extended to 13 days. Tumor necrosis was more pronounced in animals treated with hybrid.

This example demonstrated that monoclonal antibody-ricin hybrids directed against adult differentiation antigens can be effective tumor suppressive reagents in vivo. It also demonstrates that lactose which is also required to achieve selective cytotoxicity with hybrid toxins of this type can be administered as a hyperosmotic solution.

EXAMPLE 2

The cell type specificity of the toxin ricin, which ordinarily binds, enters, and kills cells through receptors containing galactose, was altered by covalently binding it to a monoclonal antibody and by reversibly binding it to lactose. The antibody, a monoclonal rat $IgG_{2b}$ directed against the Thy 1.2 antigen, provided ricin with a new binding site for the murine thymus cell surface. The addition of lactose saturated the galactose binding site on ricin and inhibited ricin from binding and killing cells via the galactose-containing receptors.

The antibody-ricin hybrid protein, anti-Thy 1.2-ricin, formed with a thioether linkage was purified by size exclusion and affinity chromatography. When assayed by inhibition of protein synthesis of EL-4 cells which express the Thy 1.2 antigen, anti-Thy 1.2-ricin was equally as toxic as ricin on a molar basis. The hybrid protein toxicity was unchanged in the presence of 100 mM lactose, whereas unmodified ricin toxicity was reduced more than 100-fold. This demonstrated the altered receptor specificity of the ricin hybrid.

The cell type specificity of the anti-Thy 1.2-ricin inhibition of protein synthesis correlated with the presence of the Thy 1.2 antigen. Anti-Thy 1.2-ricin at 4 $\mu$g/ml in the presence of lactose inhibited protein synthesis within 3.5 hours 60–80% in EL-4 cells but did not affect protein synthesis in AKR T cell lines from mice which carried the Thy 1.1 alloantigen and HeLa cells which lacked the Thy 1 antigen.

Anti-Thy 1.2-ricin in the presence of lactose selectively killed EL-4 cells at concentrations which did not kill AKR-K36 cells. This selectivity expressed as the ratio of Anti-Thy 1.2 ricin concentrations required to kill 40% of both cell types was 700.

Ricin-monoclonal antibody hybrids of this type combined a high degree of cell type selectivity and toxicity and has pharmacologic utility as anti-tumor reagents.

EXAMPLE 3

In the successful modification of ricin's native receptor and cell-type specificity to that dictated by a covalently bound monoclonal antibody, monoclonal anti-Thy 1.2 rat $IgG_{2b}$ was covalently coupled to ricin. This antibody bound to the murine T cell surface differentiation antigen which occurred in most strains with the exception of AKR and A strains. When the hybrid anti-Thy 1.2-ricin was exposed to cells in the presence of lactose, the observed toxicity exhibited cell type specificity of the antibody. Thus, anti-Thy 1.2-ricin plus lactose inhibited protein synthesis in murine T cells carrying Thy 1.2 but did not affect murine T cells of AKR background or a human cell line. Cells carrying Thy 1.2 were sensitive to a 700-fold lower concentration of Thy 1.2-ricin plus lactose than cells lacking Thy 1.2 as judged by cell killing.

EXAMPLE 4

Hybrid Synthesis

The bifunctional cross-linking agent, m-maleimidobenzoyl-N-hydroxysuccinimide ester (MBS) was used to link ricin to IgG similar to the method used to link ricin to diphtheria toxin A chain as described by Youle et al, *J. Biol. Chem.*, 254:11089–11096, 1979. Ricin, 4 mg protein in 400 μl of 0.01 M $Na_2HPO_4$, pH 7.5 was mixed while blending on a vortex miser with 13 μl of dimethylformamide containing 0.032 mg of MBS giving a molar ratio of 1.7 MBS/ricin. The mixture was incubated at room temperature for 30 min.

The monoclonal IgG against Thy 1.2 was prepared for cross-linking by partial reduction of disulfide bonds. IgG, 0.6 mg of 0.6 ml of buffered saline (as supplied from Becton Dickinson), was mixed with 30 μl of 1 M dithiothreitol and incubated at room temperature for 30 min. The IgG in 300 μl aliquots was passed over a Sephadex G-25 column (1.4×5 cm) in 6.7 mM $Na_2HPO_4$ pH 7.4 and 14 mM NaCl and the peak fractions pooled. The final volume of the pooled IgG fractions was about 3 ml containing 0.6 mg protein. The ml of partially reduced IgG was mixed with 400 μl of MBS-ricin and incubated at room temperature for 2 hours. The mole ratio of ricin:IgG was 18:1.

Hybrid Synthesis and Purification

Artificial hybrid conjugates of ricin and monoclonal antibody against the Thy 1.2 cell surface component of mouse thymus cells were synthesized with the bifunctional cross-linking agent, m-maleimidobenzoyl-N-hydroxysuccinimide as described supra. In later preparations the reaction between MBS-ricin and IgG was stopped after 2 hrs by making the mixture 6.6 mM with N-ethylmaleimide.

The hybrids were separated from unreacted ricin by high pressure liquid chromatography on a 7.5×600 mm G3000 SW TSK gel permeation column (Toyo Soda USA, 200 Park Avenue, New York, N.Y.). The column was run at a 1 ml/min flow rate with 100 mM $Na_2HPO_4$, pH 7.2. Anti-Thy 1.2 IgG was found to elute from the column after 13.4 ml and ricin after 19 ml. Chromatography of the hybrid mixture of partially reduced IgG and MBS-ricin showed a peak at 12.4 ml and another at 19 ml. Ricin eluted later than expected on the basis of molecular size presumably due to interaction with the column matrix.

The peak of hybrid protein, between 10 and 14 ml elution volume was collected from 17 runs and concentrated to 17 ml by dialysis against 60% sucrose in 6.7 mM $Na_2HPO_4$, pH 7.4, 150 mM NaCl buffer. The final concentration of protein was between 34 and 85 μg/ml.

The hybrid protein was found to the galactose residues of Sepharose-4B and thereby separated from unreacted IgG. The pooled hybrid protein and IgG fraction from the TSK column was applied to a 2 ml Sepharose-4B column, washed with 6.7 mM $Na_2HPO_4$, pH 7.4, 150 mM NaCl and the ricin-IgG hybrids eluted in a sharp peak with 100 mM lactose in the same buffer. The final yield of hybrid protein was about 95 μg of protein containing 30% of the initial IgG protein.

Hybrid Activity

The hybrid proteins, ricin and antibody were assayed for inhibition of protein synthesis in T-cell leukemic EL-4 cells which contain the Thy 1.2 antigen. The antibody alone at 4,000 ng/ml did not inhibit EL-4 cell protein synthesis. The hybrid toxin on a weight basis was 4-fold less potent than ricin and therefore on a mole basis anti-Thy 1.2-ricin equals or exceeds ricin toxicity. Lactose, which competitively blocks ricin binding to cells inhibited toxicity of ricin at least 200-fold in EL-4 cells. In contrast, the hybrid was inhibited less than 2-fold by lactose. Thus, in the presence of 100 mM lactose, EL-4 cells were more than 100-fold more sensitive to the hybrid protein than to ricin. Mixtures of equal amounts of anti-Thy 1.2 antibody and ricin behaved identically as ricin.

In the context of this invention, pharmacological amount is the pharmacological effective amount and the amount of anti Thy 1.2 monoclonal antibody-ricin is 1–3 μg.

We claim:

1. A tumor suppressive cytotoxic reagent active on murine lymphoma cancer systems which consists of anti Thy 1.2 monoclonal antibody-ricin.

2. A composition for treatment of murine neoplasma comprising a pharmacological active amount therefor of the hybrid protein anti Thy 1.2 monoclonal antibody-ricin in a hyperosmotic lactose solution.

3. A murine tumor-suppressive reagent composition comprising an effective amount therefor of the hybrid protein anti Thy 1.2 monoclonal antibody-ricin and lactose in a pharmacological carrier.

* * * * *